United States Patent [19]

Drake

[11] 4,216,169
[45] Aug. 5, 1980

[54] TWO-STAGE CATALYTIC HYDROGENATION OF OLEFINICALLY UNSATURATED DINITRILES

[75] Inventor: Charles A. Drake, Nowata, Okla.
[73] Assignee: Phillips Petroleum Company, Bartlesville, Okla.
[21] Appl. No.: 946,231
[22] Filed: Sep. 27, 1978
[51] Int. Cl.$^2$ .............................................. C07C 85/12
[52] U.S. Cl. ..................... 260/583 P; 260/465.8 R; 260/583 K
[58] Field of Search ......... 260/583 K, 583 P, 465.8 R

[56] References Cited

U.S. PATENT DOCUMENTS

| | | | |
|---|---|---|---|
| 2,532,311 | 12/1950 | Howk et al. | 260/465.8 R |
| 2,532,312 | 12/1950 | Romilly | 260/465.8 R |
| 3,161,605 | 12/1964 | Beck et al. | 252/455 |
| 3,408,397 | 10/1968 | Feldman et al. | 260/583 K |
| 3,418,375 | 12/1968 | Schmitt et al. | 260/583 P |
| 3,432,565 | 3/1969 | Kouwenhoven et al. | 260/667 |
| 3,476,793 | 11/1969 | Adam et al. | 260/465.8 R |
| 3,480,558 | 11/1969 | Lum et al. | 252/416 |
| 3,488,390 | 1/1970 | Carss et al. | 260/583 P |
| 3,591,649 | 7/1971 | Kroll et al. | 260/667 |
| 3,880,928 | 4/1975 | Drake | 260/583 K X |
| 3,880,929 | 4/1975 | Drake | 260/583 K X |
| 3,896,174 | 7/1975 | Drake | 260/583 P |
| 3,898,286 | 8/1975 | Drake | 260/583 P |
| 3,962,337 | 6/1976 | Drake | 260/583 K |
| 3,986,985 | 10/1976 | Dewdney et al. | 260/583 K |
| 4,003,933 | 1/1977 | Drake | 260/583 K |
| 4,042,629 | 8/1977 | Kershaw | 260/583 K |
| 4,053,515 | 10/1977 | Drake | 260/583 P |
| 4,140,720 | 2/1979 | Drake | 260/583 P |

FOREIGN PATENT DOCUMENTS 55959  5/1967  German Democratic Rep. ...... 260/583 K Primary Examiner—Joseph Paul Brust

[57] ABSTRACT

An olefinically unsaturated dinitrile of the formula

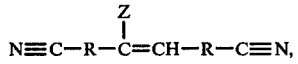

wherein each R is an alkylene or alkylidene radical and Z is an alkyl radical, is converted to the corresponding saturated dinitrile in the presence of hydrogen, a palladium catalyst and at least one alkanol having 1 to 3 carbon atoms. The saturated dinitrile is then converted to the corresponding diamine in the presence of hydrogen, a cobalt catalyst and at least one diluent selected from the group consisting of ammonia, primary alkyl amines, secondary alkyl amines, tertiary alkyl amines and mixtures of any two or more thereof. Techniques for the post calcination thermal treatment in oxygen and for the low temperature reduction of palladium catalysts prior to the hydrogenation of olefinically unsaturated dinitriles are also disclosed.

24 Claims, 1 Drawing Figure

FIG. 1

TWO-STAGE CATALYTIC HYDROGENATION OF OLEFINICALLY UNSATURATED DINITRILES

This invention relates generally to the preparation of saturated diamines by the catalytic hydrogenation of olefinically unsaturated dinitriles.

In general, various processes for the catalytic hydrogenation of unsaturated dinitriles to saturated diamines are known to those skilled in the art. Group VIII metal catalysts, such as cobalt, nickel, ruthenium, rhodium, and palladium, have been employed as effective catalysts for the hydrogenation of various feedstocks in these processes. However, it has been discovered that many of these hydrogenation catalyst materials are not always efficient or effective for the hydrogenation of unsaturated dinitriles of the formula (I)

wherein each R is an alkylene or alkylidene radical and Z is an alkyl radical. For example, U.S. Pat. No. 3,408,397 states that compounds having the formula wherein n is an integer from 1 to 12 and $R_1$ and $R_2$ are hydrogen or alkyl radicals having from 1 to 12 carbon atoms, can be hydrogenated in the presence of any of various Group VIII catalysts, including platinum, and any of various diluents, including methanol. However, it has been found that when olefinically unsaturated dinitriles of formula (I) are subjected to hydrogenation conditions in the presence of platinum and methanol, no reduction of the olefinic unsaturation is detectable. Moreover, the presence of methanol during the reduction of the dinitrile groups has been found to result in undesirable n-alkylations. It has also been found that in the hydrogenation of dinitriles of formula (I) the diluents employed can have substantial effects on catalyst activity, on catalyst life, and on the production of heavies in the form of less volatile materials remaining after distillation of the hydrogenation products.

It is an object of the invention to convert olefinically unsaturated dinitriles of formula (I) to the corresponding saturated diamines. It is a further object of the invention to achieve such conversion with a catalyst and diluent system which provides good catalyst activity, good catalyst life and good productivity. Another object of the invention is to provide an efficient process for the catalytic hydrogenation of a mixture of branched-chain unsaturated aliphatic dinitriles to produce saturated aliphatic diamines. Still another object of the invention is to provide an efficient process for the catalytic hydrogenation of branched-chain unsaturated aliphatic diamines under reaction conditions which will limit the occurrence of byproduct reactions. Other objects, aspects and advantages of the invention will be apparent from a study of the specification and the appended claims.

In accordance with the invention it has been found that these objectives can be achieved by converting the olefinically unsaturated dinitriles of formula (I) to the corresponding saturated dinitriles in the presence of hydrogen, a palladium catalyst and at least one alkanol having 1 to 3 carbon atoms, and then converting the saturated dinitriles to the corresponding diamines in the presence of hydrogen, a cobalt catalyst and at least one diluent selected from the group consisting of ammonia, primary alkyl amines, secondary alkyl amines, tertiary alkyl amines and mixtures of any two or more thereof.

Figure 1:
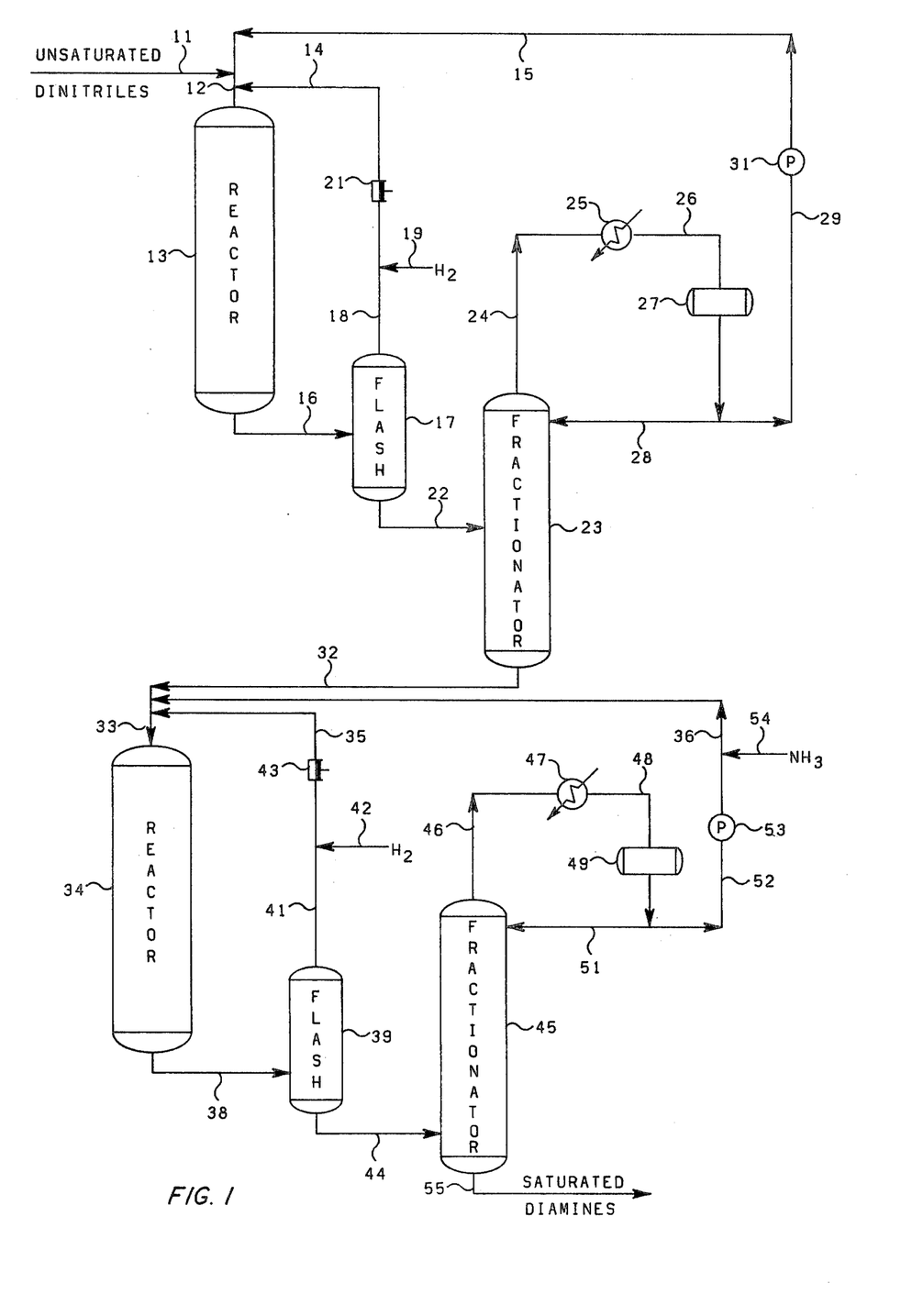

The single drawing FIGURE is a diagrammatical illustration of a process for the hydrogenation of olefinically unsaturated dinitriles embodying the present invention. In this particular embodiment, a feed stream comprising one or more suitable unsaturated dinitriles, such as branched-chain unsaturated aliphatic dinitriles, is passed through conduits 11 and 12 into a trickle bed reactor 13 along with hydrogen from conduit 14 and a diluent comprising methanol from conduit 15. The reaction 13 is operated under reaction conditions suitable for at least substantially reducing all of the olefinic unsaturation without any significant reduction of the nitrile groups. The reaction effluent, comprising saturated dinitriles, diluent and hydrogen, is passed through conduit 16 into a flash tank 17 for the recovery of the unreacted hydrogen. The hydrogen is withdrawn from flash tank 17 by way of conduit 18, combined with make-up hydrogen from conduit 19, compressed by a compressor 21 and passed through conduits 14 and 12 to the reactor 13. The liquid is withdrawn from flash tank 17 and passed by way of conduit 22 into an intermediate portion of a fractionator 23 for the removal of the diluent. The vaporous diluent is withdrawn from an upper portion of the fractionator 23 by way of conduit 24, condensed in a heat exchanger 25 and passed by way of conduit 26 into an accumulator 27. A portion of the liquid from the accumulator 27 can be passed through conduit 28 to an upper portion of the fractionator 23 as reflux, while the remaining liquid is passed through conduit 29, a pump 31 and conduits 15 and 12 to the reactor 13. The liquid dinitriles are withdrawn from a lower portion of the fractionator 23 and passed through conduits 32 and 33 into a second stage reactor 34 along with hydrogen from conduit 35, and ammonia from conduit 36.

The reactor 34 is operated under reaction conditions suitable for the conversion of at least substantially all the nitrile groups to primary amine groups and to reduce any olefinic unsaturation in the feed to the reactor 34. The effluent from the reactor 34 is passed through conduit 38 to a flash tank 39 for the recovery of the unreacted hydrogen. The hydrogen is withdrawn from the flash tank 39 by way of conduit 41, combined with make-up hydrogen from conduit 42, compressed by a compressor 43 and passed through conduits 35 and 33 to the reactor 34. The liquid is withdrawn from the flash tank 39 and passed by way of conduit 44 into an intermediate portion of a fractionator 45 for the removal of ammonia. The vaporous ammonia is withdrawn from an upper portion of the fractionator 45 by way of conduit 46, condensed in a heat exchanger 47, and passed by way of conduit 48 into an accumulator 49. A portion of the liquid from the accumulator 49 can be passed through conduit 51 to an upper portion of the fractionator 45 as reflux, while the remainder of the liquid from the accumulator 49 is passed by way of conduit 52, a pump 53 and conduit 36, along with make-up ammonia from conduit 54, into the second reactor 34. A bottoms stream comprising saturated diamines is withdrawn from a lower portion of the fractionator 45 by way of conduit 55.

Among the unsaturated dinitriles which can be advantageously and efficiently hydrogenated in accordance with the process of this invention are the branched-chain unsaturated aliphatic dinitriles of the formula $$N\equiv C-R-\overset{Z}{C}=CH-R-C\equiv N \qquad (I)$$

wherein each R is independently selected from the group consisting of alkylene radicals and alkylidene radicals, and Z is an alkyl radical. Each R will generally have from 1 to 15 carbon atoms, preferably from 1 to 6, and more preferably from 1 to 3 carbon atoms. Z will generally have from 1 to 15 carbon atoms, preferably from 1 to 6 carbon atoms, and more preferably from 1 to 3 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative unsaturated reactant species of formula (I) include such compounds as 3-methyl-3-hexenedinitrile, 3-ethyl-3-hexenedinitrile, 5-methyl-4-nonenedinitrile, 5-methyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-8-dodecanedinitrile, 2,4,7,9,11,13,15-heptaethyl-6-hexadecenedinitrile, and mixtures of any two or more thereof.

If desired, other olefinically unsaturated reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula $$N\equiv C-A-\overset{\overset{CH_2}{\|}}{C}-A-C\equiv N \qquad (II)$$

wherein each A is independently selected from the group consisting of alkylene radicals and alkylidene radicals. In general, each A will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures of any two or more thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) can be present in any suitable amount, but will generally constitute at least 0.1 weight percent of the total dinitriles. The significant advantages of the process increase with increasing concentrations of the dinitriles of formula (I) in the feedstock. Thus, the process is even more advantageous for concentrations of the dinitriles of formula (I) in the feedstock of at least 5 weight percent. The process is considered to be particularly advantageous for dinitrile feedstocks having a concentration of the dinitriles of formula (I) of at least 10 weight percent.

The presently preferred branched-chain olefinically unsaturated aliphatic dinitrile feedstock for employment in the practice of this process is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture can be any suitable value, but is generally in the range from about 10:1 to about 1:10.

The reactor 13 defines a first stage reaction zone and contains a suitable catalyst for the hydrogenation of the olefinic unsaturation, generally without significant reduction of the nitrile radical. Suitable catalysts for employment in the present invention include elemental palladium and compounds of palladium which are reducible by hydrogen under the reaction conditions of the reactor 13 to the finely divided elemental metal, and mixtures of any two or more thereof. Suitable reducible compounds include palladium oxide, palladium chloride, palladium nitrate, palladium oxalate, palladium acetate, palladium carbamate, palladium propionate, palladium tartrate, palladium hydroxide, and the like, and mixtures of any two or more thereof.

The reactor 34 defines a second stage reaction zone and contains a suitable cobalt-based catalyst for the hydrogenation of the nitrile groups and any remaining olefinic unsaturation. For example, suitable catalysts for employment in the reactor 34 include elemental cobalt and compounds of cobalt which are reducible by hydrogen under the reaction conditions in the reactor 34 to the finely divided elemental metal, and mixtures of any two or more thereof. Suitable hydrogen reducible cobalt compounds include the oxides, halides, nitrates, oxalates, acetates, carbamates, carbonates, propionates, tartrates, hydroxides, and the like and mixtures of any two or more thereof. Specific examples of suitable cobalt-based catalysts include elemental cobalt, cobalt oxide, cobalt chloride, cobalt nitrate, cobalt acetate, cobalt carbonate, cobalt carbamate, cobalt hydroxide, and mixtures of any two or more thereof.

In the practice of the first stage of this process it is often desirable to employ catalytic amounts of the elemental metal, reducible compounds of the metal catalysts or mixtures thereof supported by a solid catalyst carrier which does not deleteriously affect the catalytic hydrogenation process. Such supports include, for example, carbon, kieselguhr, silica, alumina, silica-alumina, calcium carbonate, barium carbonate, asbestos, pumice, clays, and the like, and mixtures of any two or more thereof. The elemental metal or reducible compound catalyst components can be added to the catalyst support by any of the methods well known in the art. For example, the supported catalysts can be prepared by dry mixing the components or by impregnating the support with a solution or dispersion of the metal catalyst in elemental form or in the form of reducible compounds thereof. With refractory support materials such as alumina, silica, clays, etc. the dry mixed or impregnated mixtures are calcined in air at suitable elevated temperatures, but generally in the range from about 425° to about 800° C., for a suitable period of time, but generally in the range from about 0.1 to about 50 hours. The supported catalysts can be formed into pellets, agglomerates, extrudates, powder, or other conventional physical forms before or after such calcination.

The supported catalyst can be pretreated after calcination with hydrogen to reduce the compounds, or such reduction can be achieved in the hydrogenation reactor. Any suitable amount of elemental metal catalyst can be used, but, when a support is employed, the total elemental metal catalyst will generally be in the range of about 0.01 to about 50 weight percent, and preferably in the range of about 0.1 to about 10 weight percent, based on the weight of the support. A presently preferred catalyst for the first stage reactor 13 is palladium on alumina with the palladium content being about 0.5 weight percent of the support.

While the usual method of preparation of alumina supported palladium catalysts generally involves the impregnation of the alumina with one of several palladium compounds, e.g the nitrate, acetate, the halides, etc., followed by calcination and for reduction of the resulting catalyst, it is presently preferred to employ the acetate to achieved a more active catalyst.

In the practice of the second stage of this process it is preferable to employ unsupported cobalt catalysts in the second stage reactor 34. A suitable unsupported cobalt catalyst for the second stage reaction comprises cobalt in such proportions that the catalyst contains from about 65 to about 100 weight percent cobalt.

A presently preferred unsupported cobalt catalyst for use in the second stage reactor 34 comprises a mixture of elemental cobalt and cobalt oxide in such proportions that the catalyst contains from about 70 to about 95 weight percent cobalt, and preferably from about 75 to about 90 weight percent cobalt, based on total weight of said second catalyst. A specific example of such a suitable catalyst is a commercial cobalt catalyst, Harshaw Co 1606, which contains about 80.5 weight percent cobalt, about 11.4 weight percent oxygen, about 4.2 weight percent carbon, about 0.45 weight percent calcium, about 0.1 weight percent copper, about 0.07 weight percent iron, and about 0.14 weight percent nickel.

Various promoters or activators, such as zirconium, platinum, chromium, and others known in the art, can be present in any suitable amounts, but such amounts are generally in the range from about 0.1 to about 10 weight percent of the cobalt catalyst in the reactor 34.

When associated with a refractory support such as alumina, the palladium hydrogenation catalyst in the reactor 13 can be thermally treated after calcination and before reduction to improve the stability of and retard the decline in catalytic activity during the continuous catalytic hydrogenation of the olefinic unsaturation of the unsaturated dinitriles of the hydrogenation feedstock or substrate. The thermal treatment can be conducted at temperatures broadly in the range from about 150° to about 400° C., preferably from about 200° to about 350° C., and for a suitable time sufficient to improve the stability of the catalytic activity, normally in the range from about 10 hours to about 30 hours. The thermal treatment can be conducted in any suitable oxygen-containing atmosphere, but is preferably conducted in an atmosphere containing oxygen in an amount in the range from about 1 to about 25 volume percent and at least one inert gas such as nitrogen or a mixture of inert gases in an amount in the range from about 99 to about 75 volume percent. The flow of such gas over the catalyst can be maintained at any suitable value, but such gas flow is preferably in the range from about 1 to about 100 volumes of gas per volume of supported catalyst per minute.

The palladium hydrogenation catalyst employed in reactor 13, particularly when it is associated with a support, can also be advantageously reduced in the presence of hydrogen before use in the catalytic hydrogenation of the unsaturated dinitriles of the hydrogenation substrate in the reactor 13 to obtain higher initial catalyst activity and reduce any increases in olefinic content during catalytic hydrogenation. The reduction temperature will generally be in the range from about 50° to about 200° C., and preferably in the range from about 75° to about 125° C. Any suitable pressure can be employed in the reduction of the palladium catalyst, but the reduction pressure will generally fall in the range from about atmospheric pressure to about 5000 psig (34.5 MPa), and preferably in the range from about 100 to about 3000 psig (about 0.7 to about 20.7 MPa). Any reduction time can be employed which will result in the desired degree of catalyst reduction, but generally the reduction time will be in the range from about 0.5 to about 20 hours, preferably from about 2 to about 10 hours. The hydrogen flow during the catalyst reduction can be at any suitable rate, but hydrogen flow will generally be in the range from about 0.2 to about 200 volumes of hydrogen per minute per volume of catalyst plus support, and preferably in the range from about 2 to about 100 volumes per minute per volume of catalyst plus support.

The amount of palladium catalyst employed in the hydrogenation of the carbon-to-carbon double bond for a batch process can be expressed in terms of the weight percent of catalytic palladium based on the weight of the compound being reduced. Although any suitable amount of catalyst can be employed, the amount of catalyst will generally be in the range from about 0.001 to about 30, preferably from about 0.01 to about 5 weight percent and more preferably in the range from about 0.1 to about 0.6 weight percent palladium based on the weight of hydrogenation substrate. For a continuous process, the amount of palladium catalyst will generally be such that a liquid hourly space velocity (LHSV) of from about 0.1 to about 10, preferably from about 0.5 to about 10, volumes of substrate plus diluent per volume of catalyst per hour will be attained.

The amount of cobalt catalyst employed in the second stage hydrogenation of a feedstock predominantly comprising saturated dinitriles for a batch process can be expressed in terms of the weight percent of catalytic cobalt based on the weight of the compound being hydrogenated. Although any suitable amount of catalyst can be employed, the amount of catalyst will generally be in the range of from about 0.1 to about 20, and preferably from about 0.5 to about 5 weight percent cobalt based on the weight of the hydrogenation substrate. For a continuous process, the amount of cobalt catalyst will generally be such that a liquid hourly space velocity (LHSV) of from about 0.1 to about 10, preferably from about 0.5 to about 5, volumes of substrate plus diluent per volume of catalyst per hour will be attained.

The cobalt catalyst will generally be activated before use by subjecting the catalyst to conditions suitable for activating the particular catalyst used. Typical catalyst activation conditions include a temperature in the range from about 20° to about 350° F. ($-6.7$ to about 177° C.) and a pressure in the range from about 50 to about 5000 psig (0.35 to 34.5 MPa) for a time period from about 5 minutes to about 24 or more hours in a hydrogen atmosphere.

Any catalytic hydrogenation temperature can be employed which provides the desired degree of catalytic efficiency in the hydrogenation of the unsaturated dinitrile-containing feedstock. It is desirable that the temperature in the first stage reaction be at least about 100° C., preferably at least about 120° C., and more preferably at least about 130° C. in order to provide at least substantially complete reduction of olefinic unsaturation with a reasonable catalyst life. On the other hand, it is desirable that the first stage reaction temperature be less than about 175° C., preferably less than 160° C., and more preferably less than 150° C. in order to provide a greater catalyst life and to reduce the production of heavies. Thus, the hydrogenation temperatures in the first stage will generally be within the range from about 100° to about 175° C., preferably will be within the range from about 120° to about 160° C., and more preferably will be within the range of from about 130° to about 150° C. The hydrogenation temperature in the second stage can be of any suitable value which provides the desired degree of hydrogenation, but will generally be within the range from about 25° to about 250° C., and preferably will be within the range of from about 50° to about 150° C.

The catalytic hydrogenation of the difficulty reducible carbon-to-carbon double bond illustrated in formula (I) can be carried out in the first stage at any suitable hydrogenation pressure. The catalytic hydrogenation of saturated dinitriles, such as branched chain saturated aliphatic dinitriles, can be carried out in the second stage at any suitable hydrogen pressure wherein the nitrile groups are reduced in the presence of hydrogen and wherein the feedstock and diluent are maintained substantially in the liquid state. Generally, suitable hydrogen pressures for both the first and second hydrogenation stages are within the range from about 500 to about 5000 psig (3.45 to 34.5 MPa), but lower or even higher hydrogen pressures can be employed. Preferably, due to economic considerations, hydrogen pressures within the range from about 1000 to about 3000 psig (6.9 to 20.7 MPa) are employed. It may be desirable to employ higher hydrogen pressures at lower reaction temperatures to achieve the desired degree of hydrogenation within a reasonable amount of time.

Any contact time suited for the desired catalytic hydrogenation in each stage can be employed in the practice of the present process. However, contact times economically attractive to the process are generally within the range from about 15 minutes to about 5 hours for the first stage of a batch hydrogenation process and generally within the range from about 15 minutes to about 5 hours for the second stage of the batch process. Generally, a total reaction time for both stages in the range from about 30 minutes to about 10 hours will provide suitable results, but a total reaction time in the range from about 1 to about 6 hours is presently preferred in order to insure substantially complete hydrogenation of any unsaturated olefinic bonds in the feedstock as well as complete hydrogenation of the nitrile groups to primary amino groups. The catalytic hydrogenation of unsaturated dinitriles in accordance with the present process can be carried out as a continuous process at any suitable liquid hourly space velocity. However, the liquid hourly space velocity rates will generally be within the range of from about 0.1 to about 10, more preferably from about 0.5 to about 5, volumes of dinitrile reactant plus diluent per volume of catalyst (including the volume of catalyst support if any is present) per hour.

The diluent for the first stage reaction, i.e. the reduction of the olefinic unsaturation, is composed, at least predominantly, of at least one alkanol having 1 to 3 carbon atoms. While the first stage diluent can contain a minor amount of water or other suitable codiluent, it preferably consists essentially of at least one member selected from the group consisting of methanol, ethanol, isopropanol and n-propanol, and mixtures of any two or more thereof, and more preferably consists of methanol.

The diluent for the second stage reaction, i.e. the reduction of the nitrile groups, can be any suitable diluent, but comprises generally from about 60 to about 100, and preferably from about 90 to about 100 weight percent, based on total diluent, of at least one member selected from the group consisting of ammonia, primary alkyl amines having up to 6 carbon atoms per molecule, secondary alkyl amines having up to 6 carbon atoms per molecule, and tertiary alkyl amines having up to 6 carbon atoms per molecule, and mixtures of any two or more thereof. In addition, the diluent for the second stage reaction generally comprises up to about 40, and preferably up to about 10 weight percent, based on total diluent, of at least one member selected from the group consisting of unsubstituted tertiary alkanols having from 4 to 12 carbon atoms per molecule, unsubstituted acyclic and unsubstituted cyclic ethers having from 4 to 12 carbon atoms per molecule and saturated hydrocarbons having from 4 to 12 carbon atoms per molecule, and mixtures of any two or more thereof. The term "unsubstituted" as used herein signifies that there are no substituents other than hydrocarbyl radicals. Examples of suitable tertiary alkanol diluents include 2-methyl-2-propanol, 2-methyl-2-butanol, 3-ethyl-3-hexanol, 2-ethyl-2-hexanol, 2,4-dimethyl-2-pentanol, 2,3-dimethyl-3-pentanol, 3-ethyl-3-pentanol, 3,7-dimethyl-3-octanol, 3-ethyl-3-decanol, and the like, and mixtures thereof. Examples of saturated hydrocarbons include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include 1,3-dioxane, 1,4-dioxane, tetrahydrofuran, 4,4-dimethyl-1,3-dioxane, and mixtures thereof. Examples of such alkyl amines are methylamine, dimethylamine, diethylamine, and trimethylamine. The presently preferred diluent for the second stage reaction consists essentially of ammonia.

The weight ratio of unsaturated dinitrile reactants to diluent charged to the first reaction zone can be any suitable value, however, to facilitate handling of the reaction mixtures, the weight ratio of unsaturated dinitrile reactants to diluent charged to the first reaction zone in the reactor 13 will generally be within the range from about 0.001:100 to about 35:100, and is preferably in the range from about 0.1:100 to about 25:100. Similarly, the mol ratio of diluent to dinitrile groups charged to the second reaction zone can be any suitable value, but the mol ratio of diluent to nitrile groups charged to the second reaction zone in the reactor 34 will generally be within the range from about 1:1 to about 100:1, and is preferably within the range from about 5:1 to 50:1. Water, tertiary alcohols, and hydrocarbons will not normally be present during the second hydrogenation stage of the present process, and their presence in excess of about 40 weight of the total diluent may, in some cases, adversely affect the second stage hydrogenation process.

The following examples are presented in further illustration of the invention and should not be construed in undue limitation thereof. In the examples, the olefinically unsaturated dinitriles which are being hydrogenated are a mixture obtained by the reaction of isobutylene and acrylonitrile. This unsaturated dinitrile mixture comprises 5-methyl-4-nonenedinitrile, 2,4-dimethyl-4-ctenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, this mixture will be described in the examples as diadduct. This diadduct can be hydrogenated to produce a valuable saturated diamine for use in the preparation of polyamides and other polymers. In such applications, it has been found to be highly desirable that essentially none of the olefinic unsaturation remains in the final hydrogenation product and that the final hydrogenation product be at least substantially free of N-alkyl groups. Thus, it is important that the carbon-carbon olefinic double bonds and the nitrile groups in the diadduct be reduced efficiently in the hydrogenation process employed.

EXAMPLE I

In each of a series of batch runs, 30 grams of diadduct, 350 milliliters of diluent and the indicated amount and type of catalyst were introduced into a one-liter autoclave. The autoclave was pressured to about 500 psig (3.45 MPa) with nitrogen, vented and this process repeated before pressuring the vessel with hydrogen to about 1500 psig (10.35 MPa). The pressure was maintained at about 1500 psig (10.35 MPa) by repressuring with hydrogen as necessary. In each run the catalyst consisted of about 5 weight percent of the indicated metal on high surface area alumina powder. The reaction time in each run was about 2 hours. Other conditions and results are set forth in Table I.

TABLE I

| Run | Catalyst Type | Amount, g. | Weight Ratio[a] | Diluent | Temp., °C. | Results[b] |
|---|---|---|---|---|---|---|
| 1 | palladium | 5 | 0.83 | t-butanol | 75 | 10% unsaturation |
| 2 | palladium | 3 | 0.50 | t-butanol | 150 | complete reduction |
| 3 | palladium | 2 | 0.33 | t-butanol | 130 | Trace unsaturation |
| 4 | palladium | 2 | 0.33 | methanol | 150 | complete reduction |
| 5 | palladium | 2 | 0.33 | methanol | 130 | complete reduction |
| 6 | palladium | 1 | 0.17 | methanol | 100 | 10% unsaturation |
| 7 | palladium | 1 | 0.17 | methanol | 150 | 2% unsaturation |
| 8 | palladium | 3 | 0.50 | methanol | 150 | no reduction |

[a]grams of catalyst, calculated as elemental catalytic methal (palladium or platinum) per 100 grams of diadduct.
[b]The percentage unsaturation or reduction is based only on the olefinic unsaturation.

The data of Table I demonstrates that palladium is an effective catalyst for the hydrogenation of the olefinic unsaturation in diadduct whereas platinum is not effective in the presence of methanol.

EXAMPLE II

Each of a series of continuous reaction runs was conducted with a fixed catalyst bed, a feed of about 10 weight percent diadduct in the indicated diluent, a liquid hourly space velocity of diadduct/diluent mixture of about 1 volume of diadduct plus diluent per volume of catalyst (including the volume of catalyst support if any is present) per hour, and a hydrogen flow of about 1 liter per minute (about a 100 fold excess) at an operating pressure of about 1500 psig (10.35 MPa). Unless otherwise indicated each catalyst was about 0.5 weight percent of the indicated catalytic metal on 6–14 mesh chi-alumina. Other conditions and results are set forth in Table II.

TABLE II

| Run | Catalyst | Diluent | Temp., °C. | Catalyst Life, Hrs. | Heavies[g] Wt. % | Remarks |
|---|---|---|---|---|---|---|
| 9 | palladium | methanol | 60 | 20 | ND | 10% unsaturation |
| 10 | palladium | methanol | 100–110 | 300 | 2 | complete reduction |
| 11 | palladium | methanol | 140 | >1200 | 2.5 | complete reduction |
| 12 | Pd—Cr[a] | methanol | 100 | 20 | ND | polymer |
| 13 | Pd—Pt[b] | methanol | 120 | 50 | ND | little reduction |
| 14 | palladium | t-butanol | 150 | 250 | 8 | declining activity |
| 15 | palladium | t-butanol | 100–125 | 300 | 5 | declining activity |
| 16 | palladium | [e] | 110 | 250 | 4 | declining activity |
| 17 | palladium | [f] | 150–160 | 100 | 13 | declining activity |

TABLE II-continued

| Run | Catalyst | Diluent | Temp., °C. | Catalyst Life, Hrs. | Heavies[g] Wt. % | Remarks |
|---|---|---|---|---|---|---|
| 18 | palladium | toluene | 100–140 | 120 | ND | declining activity |
| 19 | rhenium[c] | methanol | 100–150 | [h] | ND | no reaction |
| 20 | palladium[d] | toluene | 100–120 | 120 | ND | declining activity |

[a]about 0.5 wt % palladium and about 0.5 wt % chromium on chi-alumina powder.
[b]about 0.5 wt % palladium and about 0.1 wt % platinum on chi-alumina powder.
[c]about 0.5 wt % rhenium on ⅛" chi-alumina pellets.
[d]about 0.5 wt % palladium on 1/16" chi-alumina pellets.
[e]a 50/50, by weight, mixture of t-butanol and cyclohexane.
[f]a mixture of olefinically saturated dinitriles obtained from previous hydrogenation of diadduct.
[g]ND - not determined.
[h]No reaction.

The results of Table II agree with those found in the batch study shown by Table I, in that, of the catalysts examined in these runs, palladium was the only effective catalyst for the hydrogenation of the double bonds of diadduct. Rhenium, a catalyst noted for its resistance to deactivation by poisons, was inactive and palladium catalysts modified with chromium or platinum were deactivated.

Methanol was clearly the best diluent examined, both from the standpoint of catalyst life and heavies formation. A catalyst life of at least 1200 hours was observed with methanol with only 2 percent heavies (the catalyst life was certainly greater but the test was interrupted after 1200 hours for physical examination of the catalyst which was in good shape). Although methanol appears to be an ideal diluent, previous work has shown that it gives n-alkylation in the nitrile reduction step. Therefore, complete removal of methanol would be required before the second stage reaction step. However, with t-butanol only fair results were obtained with a catalyst life of about 250–300 hours and several times more heavies than with methanol. To circumvent one possible process problem of t-butanol alcohol, i.e., the high freezing point of 78° F. (25.5° C.), a mixture of t-butyl alcohol and cyclohexane (F.P. −10° F. or −23.2° C.) was tested in Run 16. The catalyst life was about the same as with t-butyl alcohol but heavies were slightly less. Toluene seemed to be the poorest diluent with a short catalyst life combined with rapidly declining activity. Although not normally thought of as a diluent, olefinically saturated diadduct was examined as a hydrogenation diluent in Run 17. This technique would eliminate the necessity of diluent removal and simplify operation. However, the catalyst life with this diluent was short and heavies were unacceptably high. Of the three best diluent systems, the most rapid rise in temperature required for complete reduction is observed with the t-butyl alcohol-cyclohexane system, followed rather closely by t-butyl alcohol. Methanol rises much less rapidly and levels off at about 140° C. and gives a reasonable catalyst life of at least about >1200 hours. Table II shows that a temperature of at least 100° C. was necessary for complete reduction (although a lower temperature would certainly give lower heavies and probably longer catalyst life). All of the diluents tested other than methanol required a gradual temperature increase from about 100° C. up to a temperature in the range from about 150° to about 160° C. over the life of the catalyst to maintain complete saturation. Temperatures above about 160° C. gave unacceptably high heavies and plugging of catalyst bed. The temperature rise necessary to maintain complete reduction with methanol appeared limited to about 140° C. The entire study was conducted at 1500 psig (10.35 MPa) although a higher pressure should give increased catalyst life, a lower reaction temperature, and reduced heavies.

The palladium catalysts can be regenerated by the removal of all organic material by oxidation, conversion of the palladium to the oxide, and reduction back to the active state; e.g. an air burnoff using a mixture of about 20 percent air and about 80% nitrogen at a temperature in the range from about 371° to about 427° C. followed by reduction at about 177° C. gave activity equal to fresh catalyst. This cycle (operation for about 300 hours followed by burnoff and reduction) has been repeated four times with excellent results.

EXAMPLE III

A series of thirteen runs was made using a ½-inch (12.7 millimeter) diameter×20-inch (508 millimeter) length laboratory continuous reactor. A cobalt catalyst, Co 1606, was charged to the reactor and reduced with hydrogen at a temperature and pressure suitable for the catalyst used. The Co 1606 cobalt catalyst is a commercial amination catalyst available from Harshaw Chemical Company. Co 1606 catalyst is a cobalt/cobalt oxide catalyst which contains about 80.5 weight percent cobalt, about 11.4 weight percent oxygen, about 4.2 weight percent carbon, about 0.45 weight percent calcium, about 0.1 weight percent copper, about 0.07 weight percent iron, and about 0.14 weight percent nickel. The Co 1606 catalyst has a surface area of about 16 m²/g and a pore volume (below 600 Å in diameter) of about 0.12 cc/g. The reactor temperature and hydrogen pressure were adjusted to the values desired for the hydrogenation and a mixture of diadduct and diluent was fed continuously with hydrogen to the reactor. The hydrogenation product was analyzed by gas-liquid chromatography after the diluent was removed by distillation at atmospheric or reduced pressure. The amount of heavies present in the hydrogenation product was determined by distillation of the product and measuring the weight of the pot residue. The percent of heavies was calculated based on the total hydrogenation product weight following diluent removal. Although the cobalt catalyzed second stage hydrogenation of the present invention is intended for the hydrogenation of nitrile groups, the diadduct (a mixture of olefinically unsaturated dinitriles) was used as the hydrogenation substrate in Example III due to its availability. The olefinic unsaturation was incompletely hydrogenated and was not considered in the product analysis.

Runs 21 through 25 were conducted with ammonia as the only diluent and with an unsupported cobalt catalyst (Co 1606). Run 21 continued for about 1246 hours before the catalyst bed formed a plug, and Run 24 continued for about 308 hours at a LHSV of about 2 before the catalyst began to peel. The 308 hour run time at a LHSV of about 2 for Run 24 corresponds to a run time of about 600 hours at a LHSV of about 1. The catalyst in Run 23 began to collapse after about 212 hours running time at a LHSV of about 2. However, it should be noted that a lower pressure was employed in Run 23 which is known to give a shorter catalyst life. Run 25 utilized a lower temperature and a higher pressure then were utilized in Runs 21 through 24 and the catalyst was unchanged after about 500 hours running time at a LHSV of about 2.

Runs 26 and 27 (supported cobalt catalyst with ammonia as diluent) and Run 28 (supported nickel catalyst with ammonia as a diluent) had very short catalyst lives compared with Run 21. In Run 29, the catalyst was the nickel counterpart of Co 1606 and was an unsupported mixture of nickel and nickel oxide containing about 80 weight percent nickel. The catalyst plugged in the reactor after only about 7 hours.

Therefore, the data adduced in Runs 21 through 29 show that supported or unsupported nickel catalysts and supported cobalt catalysts do not give the long life in an ammonia diluent that is provided by an unsupported cobalt catalyst.

Other common diluents such as benzene (Run 30), t-butyl alcohol (Run 31), and mixtures of t-butyl alcohol and cyclohexane (Run 33), with low levels of ammonia as a suppressant of secondary amine formation, resulted in catalyst decomposition, plugging, or lack of activity with Co 1606 catalyst after only about 90 to about 170 hours of running time at a LHSV of 2. Methanol is not given as an example of a diluent since methanol is known to cause n-methylation of the dinitriles during hydrogenation which results in poor fiber properties in polyamides made from the diamine. In Run 32, low levels of t-butyl alcohol and cyclohexane were present with a large quantity of ammonia, and after about 172 hours of running time the catalyst had started to flake but no nitrile unsaturation had appeared in the product.

Table III presents the catalyst, diluents, conditions, and results of these runs.

TABLE III

| Run No. | Catalyst | Diluent | Weight Ratio[f] DA/Other diluent(s)NH$_3$ | Temp., °C. | Pressure,[a] psig | Rate[b] | Heavies % | Reaction Stopped, Hours | Remarks |
|---|---|---|---|---|---|---|---|---|---|
| 21 | Co 1606 | NH$_3$ | 1/0/9 | 100 | 1500 | 1 | 2.8 | 1246 | reactor plugged |
| 22 | Co 1606 | " | 1/0/9 | 100 | 1500 | 1 (216 hrs) 2 (165 hrs) | ND[d] | 381 | beginning of catalyst decomp. |
| 23 | Co 1606 | " | 1/0/9 | 100 | 500 | 2 | ND | 212 | beginning of cat. collapse |
| 24 | Co 1606 | " | 1/0/9 | 100 | 1500 | 2 | 2.0 | 308 | cat. beginning to peel |
| 25 | Co 1606 | " | 1/0/9 | 75 | 2500 | 2 | 0.76 | 500 | catalyst OK |
| 26 | 65% Co on Kieselguhr | " | 1/0/4 | 130 | 1500 | 1 | ND | 23 | reactor plugged |
| 27 | 60% Co on Kieselguhr | " | 1/0/9 | 120 | 1500 | 1 | ND | 4 | very low cat. |
| 28 | 40% Ni on chi-alumina | " | 1/0/4 | 130 | 1500 | 1 | ND | 23 | reactor plugged |
| 29 | Ni[c] | " | 1/0/9 | 80 | 2500 | 2 | ND | 7 | reactor plugged |
| 30 | Co 1606 | Benzene, NH$_3$ | 1/9/2 | 100 | 1500 | 2 | 0.9 | 96 | cat. beginning to decomp. |
| 31 | Co 1606 | t-BuOH, NH$_3$ | 1/9/2 | 80 | 2500 | 2 | ND | 118 | —CN unsatura. appears[e] |
| 32 | Co 1606 | t-BuOH, Cyclohexane, NH$_3$ | 1/0.225/0.225/8.55 | 100 | 1500 | 2 | ND | 172 | cat. beginning to flake |
| 33 | Co 1606 | t-BuOH, Cyclohexane, NH$_3$ | 1/2.8/4.2/2 | 100 | 1500 | 2 | 1.3 | 167 | reactor plugged —CN unsatura. appears[e] |

[a] 500 psig = 3.45 MPa  1500 psig = 10.34 MPa  2500 psig = 17.24 MPa
[b] Rate = LHSV
[c] Prepared to be similar to Co 1606.
[d] ND = not determined.
[e] Catalyst activity decreased to level where nitrile hydrogenation is incomplete.
[f] DA = diadduct.

EXAMPLE IV

Two runs were conducted in which the olefinic unsaturation of diadduct was hydrogenated in a 0.5 inch (12.7 millimeter) diameter×20-inch (508 millimeter) long laboratory continuous reactor in the presence of palladium catalysts. In each run, the palladium catalyst was Girdler T-1370 catalyst containing about 0.5 weight percent palladium based on the weight of the alumina support. In Run 34, about 120 milliliters of the catalyst was subjected to a thermal treatment at about 300° C. for about 20 hours in a gaseous stream containing about 5 volume percent oxygen and about 95 volume percent nitrogen at a flow rate of about 1 liter per minute. In Run 35, such a separate thermal treatment was omitted from the same quantity of catalyst. In both runs the catalyst was reduced at about 150° C. and about 1500 psig (10.3 MPa) for about 4 hours with a hydrogen flow rate of about 1 liter per minute. The hydrogenation conditions for the hydrogenation of diadduct were about 100° C., about 1500 psig (10.3 MPa), and about 1 liter per minute hydrogen flow rate. The feed stream of the hydrogenation reaction zone contained about 10 weight percent diadduct and about 90 weight percent methanol and was fed to the reactor at a LHSV of about 3. The results of these runs are shown in Table IV.

TABLE IV

| Run No. | Catalyst Thermal Treatment[a] Temp., °C | Time, hrs. | Diadduct Hydrogenation Olefinic Content of Product[b], weight % | | |
|---|---|---|---|---|---|
| | | | 3 hours | 18 hours | 42 hours |
| 34 | 300° | 20 | 0.5 | 1.5 | 4.2 |
| 35 | no treatment | | 0.6 | 4.3 | (c) |

[a]Treatment of catalyst before reduction.
[b]Olefinic unsaturation in the hydrogenation product at the indicated time in the run.
[c]This run was terminated after 18 hours.

The thermal treatment used for the palladium catalyst in Run 34 resulted in a smaller increase in olefinic content in the product of the hydrogenation of diadduct than was provided by the untreated catalyst of Run 35. The results of these runs demonstrate the value of the thermal treatment of the catalyst before reduction for improving the stability of the catalytic activity during hydrogenation.

EXAMPLE V

Three runs were conducted in which the olefinic unsaturation of diadduct was hydrogenated in the presence of palladium catalysts identical to the catalysts (Girdler T-1370) of Example IV. Each of the three runs was given a different reduction treatment. Catalyst reduction and diadduct hydrogenation was performed in a 0.5 inch (12.7 millimeter) diameter×20-inch (508 millimeter) long laboratory continuous reactor in each of the three runs. In each of the three runs the catalyst reductions were performed at about 1500 psig (10.3 MPa) with a hydrogen flow rate of about 1 liter per minute. In Run 36, the catalyst reduction temperature was about 100° C. and the run time was about 4 hours. In Run 37 the catalyst reduction temperature was about 150° C. and the run time was about 4 hours. In Run 38 the catalyst reduction temperature was about 300° C. and the run time was about 3 hours. In each of the three runs, the hydrogenation conditions were about 100° C., about 1500 psig (10.3 MPa) pressure, and about 1 liter per minute hydrogen flow rate. The hydrogenation feed stream contained about 10 weight percent diadduct and about 90 weight percent methanol and was fed to the hydrogen reactor at a LHSV of about 3 in each of the three runs. The catalyst reduction conditions and hydrogenation results are shown in Table V.

TABLE V

| Run No. | Catalyst Reduction Temp., °C | Time, hrs. | Diadduct Hydrogenation Olefinic Content of Product[a], weight % | |
|---|---|---|---|---|
| | | | 3 hours | 18 hours |
| 36 | 100 | 4 | 0.4 | 1.8 |
| 37 | 150 | 4 | 0.6 | 4.3 |
| 38 | 300 | 3 | 5.0 | 13.3 |

[a]Olefinic unsaturation in hydrogenation product at indicated time in the run.

The results of these three runs show that the catalyst reduction temperature is important for both initial catalyst activity, as indicated by olefinic unsaturation present in the hydrogenation product after 3 hours with low levels indicating high catalytic activity, and change in catalytic activity with time, as evidenced by the difference in olefinic unsaturation present in samples collected after about 3 hours and after about 18 hours with small differences indicating small changes in catalytic activity. Run 38, which involved a catalyst reduction temperature of about 300° C., had a low initial activity and an increase in olefinic content of 8.2 between sampling times, while Runs 36 and 37, which involved lower catalyst reduction temperatures of about 100° C. and about 150° C., respectively, had higher initial activity and lower increases in olefinic content between sampling times than were provided by Run 38.

Reasonable variations and modifications to the invention are possible within the scope of the foregoing disclosure and the appended claims.

What is claimed is:

1. A process for the catalytic hydrogenation of an olefinically unsaturated dinitrile feedstock comprising at least one unsaturated dinitrile compound of the formula wherein each R is independently selected from the group consisting of alkylene radicals and alkylidene radicals, Z is an alkyl radical, and the number of carbon atoms in said compound is in the range from 7 to 30; which process comprises:

(a) contacting said feedstock in a first stage reaction zone with hydrogen, a first diluent and a first catalyst under suitable first stage hydrogenation conditions to thereby effect the at least substantially complete hydrogenation of the olefinic unsaturation of said compound, said diluent comprising at least one member selected from the group consisting of alkanols having 1 to 3 carbon atoms, said first catalyst comprising at least one catalytic component selected from the group consisting of elemental palladium, compounds of palladium which are reducible by hydrogen to elemental palladium at said suitable first stage hydrogenation conditions and mixtures of any two or more thereof, so as to form a first reaction effluent;

(b) removing said first diluent from said thus formed first reaction effluent so as to form an intermediate dinitrile product at least substantially free of olefinic unsaturation and at least substantially free of said alkanols;

(c) contacting said thus formed intermediate dinitrile product in a second stage reaction zone with hydrogen, a second diluent, and a second catalyst under suitable second reaction conditions to thereby effect the at least substantially complete conversion of the nitrile groups in said intermediate dinitrile product to primary amine groups; said second diluent being at least substantially free of any component having an adverse effect on the hydrogenation of said nitrile groups and being composed of from about 60 to about 100 weight percent of at least one member selected from the group consisting of ammonia, primary alkyl amines, secondary alkyl amines, tertiary alkyl amines and mixtures of any two or more thereof, based on total second diluent; and said second catalyst comprising at least one unsupported catalytic component selected from the group consisting of elemental cobalt, compounds of cobalt which are reducible by hydrogen to elemental cobalt at said suitable second stage reaction conditions, and mixtures of any two or more thereof, so as to form a second reaction effluent.

2. A process in accordance with claim 1 further comprising removing at least a substantial portion of unreacted hydrogen and at least a substantial portion of the second diluent from the thus formed second reaction effluent so as to provide a diamine product essentially free of olefinic unsaturation and nitrile groups.

3. A process in accordance with claim 2 further comprising recycling the thus removed first diluent to said first stage reaction zone, and recycling the thus removed second diluent to said second stage reaction zone.

4. A process in accordance with claim 1 wherein said first diluent consists essentially of methanol.

5. A process in accordance with claim 1 wherein said first catalyst consists essentially of at least one catalytic component selected from the group consisting of elemental palladium, compounds of palladium which are reducible by hydrogen to elemental palladium at said suitable hydrogenation conditions and mixtures of any two or more thereof and a support, and wherein said second catalyst consists essentially of at least one catalytic component selected from the group consisting of elemental cobalt, compounds, of cobalt which are reducible by hydrogen to elemental cobalt at said suitable reaction conditions and mixtures of any two or more thereof.

6. A process in accordance with claim 1 wherein said second diluent comprises from about 90 to about 100 weight percent of at least one member selected from the group consisting of ammonia, primary alkyl amines, secondary alkyl amines, tertiary alkyl amines and mixtures of any two or more thereof, based on total second diluent.

7. A process in accordance with claim 1 wherein said second diluent comprises from about 90 to about 100 weight percent ammonia, based on total second diluent.

8. A process in accordance with claim 1 wherein said second diluent consists essentially of ammonia.

9. A process in accordance with claim 7 wherein said at least one unsaturated dinitrile compound comprises a mixture of 5-methyl-4-nonenedinitrile, 2,4-dimethyl-4-octenedinitrile, 2,4-dimethyl-3-octenedinitrile, and 2,4,6-trimethyl-3-heptenedinitrile.

10. A process in accordance with claim 7 wherein said olefinically unsaturated dinitrile feedback further comprises at least one unsaturated dinitrile reactant of the formula wherein each A is independently selected from an alkylene radical and an alkylidene radical, and the number of carbon atoms per molecule of said reactant is in the range from 7 to 30.

11. A process in accordance with claim 10 wherein the weight ratio of the elemental catalytic palladium present in said first stage reaction zone to the dinitriles in the feedback charged to said first stage reaction zone is in the range from about 0.001:100 to about 30:100, the weight ratio of the elemental catalytic cobalt present in second stage reaction zone to the dinitriles in the feedstock charged to said second stage reaction zone is in the range from about 0.01:100 to about 20:100, the hydrogen pressure in each of said first and second stage reaction zones is in the range from about 500 to about 5000 psig (3.45 to 34.5 MPa), the weight ratio of the unsaturated dinitriles in the feedstock charged to said first stage reaction zone to the diluent in said first reaction zone is in the range of about 0.001:100 to about 15:100, wherein the mol ratio of diluent in said second stage reaction zone to the nitrile groups charged to said second stage reaction zone is in the range of about 1:1 to about 100:1, wherein the temperature in said first stage reaction zone is in the range of about 100° C. to about 175° C., wherein the temperature in said second stage reaction zone is in the range of about 25° C. to about 250° C., and wherein the reaction time for each of said first and second stage reaction zones in a batch process is in the range of from about 15 minutes to about 5 hours and the liquid hourly space velocity rate in each of said first stage reaction zone and said second stage reaction zone in a continuous process is in the range of about 0.1 to about 10 volumes of dinitrile plus diluent per volume of catalyst per hour.

12. A process in accordance with claim 1 wherein the weight ratio of the elemental catalytic palladium present in said first stage reaction zone to the dinitriles in the feedstock charged to said first stage reaction zone is in the range from about 0.001:100 to about 30:100, the weight ratio of the elemental cobalt present in second stage reaction zone to the dinitriles in the feedstock charged to said second stage reaction zone is in the range from about 0.01:100 to about 20:100, the hydrogen pressure in each of said first and second stage reaction zones is in the range from about 500 to about 5000 psig (3.45 to 34.5 MPa), the weight ratio of the unsaturated dinitriles in the feedstock charged to said first stage reaction zone to the diluent in said first reaction zone is in the range of about 0.001:100 to about 15:100, wherein the mol ratio of diluent in said second stage reaction zone to the nitrile groups charged to said second stage reaction zone is in the range of about 1:1 to about 100:1, wherein the temperature in said first stage reaction zone is in the range of about 100° C. to about 175° C., wherein the temperature in said second stage reaction zone is in the range of about 25° C. to about 250° C., and wherein the reaction time for each of said first and second stage reaction zones in a batch process is in the range of from about 15 minutes to about 5 hours and the liquid hourly space velocity rate in each of said first stage reaction zone and said second stage reaction zone in a continuous process is in the range of about 0.1 to about 10 volumes of dinitrile plus diluent per volume of catalyst per hour.

13. A process in accordance with claim 1 wherein the temperature in said first stage reaction zone is in the range from about 100° C. to about 175° C. and wherein the temperature in said second stage reaction zone is in the range from about 25° C. to about 250° C.

14. A process in accordance with claim 1 wherein the temperature in said first stage reaction zone is in the range from about 130° C. to about 150° C. and wherein the temperature in said second stage reaction zone is in the range from about 50° C. to about 150° C.

15. A process in accordance with claim 1 wherein the temperature in said first stage reaction zone is in the range from about 120° C. to about 160° C. and wherein the temperature in said second stage reaction zone is in the range from about 25° C. to about 250° C.

16. A process in accordance with claim 15 wherein said first diluent consists essentially of methanol.

17. A process in accordance with claim 16 wherein said first catalyst consists essentially of at least one catalytic component selected from the group consisting of elemental palladium, compounds of palladium which are reducible by hydrogen to elemental palladium at said suitable hydrogenation conditions and mixtures of any two or more thereof and a support, and wherein said second catalyst consists essentially of at least one catalytic component selected from the group consisting of elemental cobalt, compounds of cobalt which are reducible by hydrogen to elemental cobalt at said suitable reaction conditions and mixtures of any two or more thereof.

18. A process in accordance with claim 1 wherein said second catalyst comprises an unsupported mixture of elemental cobalt and cobalt oxide, said second catalyst containing from about 70 to about 95 weight percent cobalt, based on total weight of said second catalyst.

19. A process in accordance with claim 18 wherein said second diluent consists essentially of ammonia.

20. A process in accordance with claim 19 wherein the temperature in said second stage reaction zone is in the range of from about 25° C. to about 250° C.

21. A process in accordance with claim 1 wherein said first catalyst is contacted prior to step (a) with a gaseous stream consisting essentially of oxygen and at least one inert gas at a temperature in the range from about 150° C. to about 400° C. and at a gas flow rate in the range from about 1 to about 100 volumes of gas per volume of said first catalyst per minute for a time sufficient to improve the stability of catalytic activity during step (a).

22. A process in accordance with claim 21 wherein said gaseous stream consists essentially of oxygen in the range from about 1 to about 25 volume percent and at least one inert gas in the range from about 99 to about 75 volume percent, and wherein said first catalyst is contacted with said gaseous stream at a temperature in the range from about 200° to about 350° C. and for a time period in the range of from about 10 to about 30 hours.

23. A process in accordance with claim 1 wherein said first catalyst is contacted prior to step (a) with hydrogen at a reduction temperature in the range from about 50° C. to about 200° C., at a reduction pressure in the range from about atmospheric to about 5000 psig (34.5 MPa), at a hydrogen flow rate in the range from about 0.2 to about 200 volumes of hydrogen per minute per volume of catalyst plus support, and for a time period in the range from about 0.5 to about 20 hours, so as to obtain higher initial catalyst activity and to reduce any increases in olefinic content during step (a).

24. A process in accordance with claim 23 wherein said reduction temperature is in the range from about 75° C. to about 125° C.

* * * * *

UNITED STATES PATENT AND TRADEMARK OFFICE
CERTIFICATE OF CORRECTION

PATENT NO. : 4,216,169

DATED : August 5, 1980

INVENTOR(S) : Charles A. Drake

It is certified that error appears in the above-identified patent and that said Letters Patent are hereby corrected as shown below:

Column 17, claim 10, line 45, after "dinitrile" and before "further" change "feedback" to --- feedstock ---.

Column 17, claim 11, line 59, after "the" and before "charged" change "feedback" to --- feedstock ---.

Signed and Sealed this

Seventh Day of April 1981

[SEAL]

Attest:

RENE D. TEGTMEYER

Attesting Officer     Acting Commissioner of Patents and Trademarks